United States Patent [19]

Purvis et al.

[11] Patent Number: 4,655,077

[45] Date of Patent: Apr. 7, 1987

[54] WEAR SENSOR SYSTEM

[76] Inventors: Howard A. Purvis; Robert F. Stricker, both of P.O. Box 79286, Houston, Tex. 77279

[21] Appl. No.: 739,899

[22] Filed: May 31, 1985

[51] Int. Cl.⁴ .............................................. G01N 17/00
[52] U.S. Cl. ........................................................... 73/86
[58] Field of Search .............. 73/86, 7; 340/540, 605, 340/550; 138/36

[56] References Cited

U.S. PATENT DOCUMENTS

| | | | |
|---|---|---|---|
| 2,110,079 | 3/1938 | Butler | 138/36 |
| 2,991,439 | 7/1961 | Marsh et al. | 73/86 |
| 3,078,707 | 2/1963 | Weaver | 73/7 |
| 3,307,401 | 3/1967 | Bachman | 73/86 |
| 3,532,797 | 10/1970 | Lunig | 73/86 |
| 4,442,706 | 4/1984 | Kawate et al. | 73/86 |
| 4,448,062 | 5/1984 | Peterson et al. | 73/86 |

Primary Examiner—Stewart J. Levy
Assistant Examiner—Robert R. Raevis
Attorney, Agent, or Firm—Glaser, Griggs & Schwartz

[57] ABSTRACT

A wear sensor system for detecting erosion, corrosion and wear of a component is disclosed. Conductive loops of a sensor probes are embedded at spaced locations through the component. As erosion, corrosion or wear of the component is sustained, each conductive loop is subjected to such wear condition in turn and is interrupted only as the component is worn away at its particular location. The continuity status of each loop is evaluated periodically, with an electrical closed circuit condition indicating structural integrity at that particular loop location, and an electrical open circuit condition indicating such a wear condition.

1 Claim, 8 Drawing Figures

WEAR SENSOR SYSTEM

FIELD OF THE INVENTION

This invention relates generally to wear sensor apparatus, and in particular to devices for detecting erosion, corrosion and wear.

BACKGROUND OF THE INVENTION

Processing steps in refineries or other manufacturing plants frequently involve erosive fluid streams. For example, in a fluid catalytic cracking process, valves are exposed to the erosive forces of high temperature gases and/or solids entrained therein. The impact of fluid entrained particles flowing at high velocities tends to erode valve components projecting into the fluid stream. Indeed, many internal components are subject to the effects of erosion, corrosion and wear.

The valves most commonly used in high temperature gas applications are slide valves and plug valves. These valves feature single or multiple slides or plugs operating in a plane generally perpendicular or parallel to the direction of fluid flow, thereby controlling flow, as needed. These valves also employ an orifice section which may be located upstream or downstream of the slide or plug depending upon the design employed. The orifice edges as well as the edges of the slides or plugs exposed to the fluid flow frequently experience severe erosion. To prevent damage to costly valve components and flowlines, a refractory liner shields the inner valve surfaces which are most likely to experience the effects of such erosion, corrosion and wear.

DESCRIPTION OF THE PRIOR ART

Such high temperature valves and flowlines must be inspected and repaired from time to time to avoid a catastrophic failure due to the effects of component erosion and wear. Presently, it is necessary to shut down the production operation while critical components such as the high temperature valve and its refractory lining are inspected and repaired or replaced. Because of the consequences of a catastrophic failure, such maintenance operations have been scheduled relatively frequently, resulting in a substantial loss of production. In the past, the frequency of such overhaul operations has been based upon operational experience and the timing of a shut-down has depended to a large extent upon personal judgement.

It will be appreciated that it is desirable to continue production operations as long as possible between maintenance shut-downs. To be cost effective, shut-downs are scheduled at a frequency as close to the optimum (longest run to least cost) as possible. The optimum shut-down time is presently not predictable with precision, therefore the shut-down of such units for inspection and repair is scheduled on the safe side of the predicted optimum frequency to avoid catastrophic damage.

Since shut-down in a refining or similar fluid flow process can be very costly, it is desirable to maximize the available on-stream time of high temperature valves, flowlines, and the like.

SUMMARY OF THE INVENTION

A new and improved wear sensor system of this invention provides erosion and wear information that will allow production runs to be extended to their maximum without risk of damaging costly components and the like, and provides real time information which permits the operator to react to an incipient component failure that would force an unscheduled shut-down.

At the heart of this new and improved wear sensor system is a wear sensor probe which includes one or more conductive loops embedded within a liner component which is exposed to the effects of erosion and wear within or at the boundary of a fluid flow stream. In this arrangement, each conductive loop includes a wearable conductive portion embedded at a particular location within the liner component. In a preferred embodiment, an array of conductive loops are provided with the wearable conductive portions being embedded at spaced locations through the body of the liner component.

The liner integrity or wear condition is indicated by the electrical closed circuit or open circuit condition of each conductive loop. That is, as erosion or wear of the liner structure is sustained, each conductive loop is subjected to erosion in turn and is interrupted only as the liner component structure is worn away at its particular location. The continuity status of each loop is evaluated periodically, with an electrical closed circuit condition indicating structural integrity at that particular loop location, and an electrical open circuit condition indicating liner erosion at that particular loop location.

In a preferred embodiment, the continuity status of each wear sensor probe is converted to logic one and logic zero digital data information which is sampled periodically by a central processing unit (CPU) for providing a visual or audible indication in response to a predetermined erosion or wear condition. Additionally, the CPU is programmed to analyze collected wear data and, under the direction of a controller, projects component and system failures as a function of time.

The novel features which characterize the invention are defined by the appended claims. The foregoing and other objects, advantages and features of the invention will hereinafter appear, and for purposes of illustration of the invention, but not of limitation, an exemplary embodiment of the invention is shown in the appended drawings.

DETAILED DESCRIPTION OF THE PREFERRED EMBODIMENTS

Figure 1:
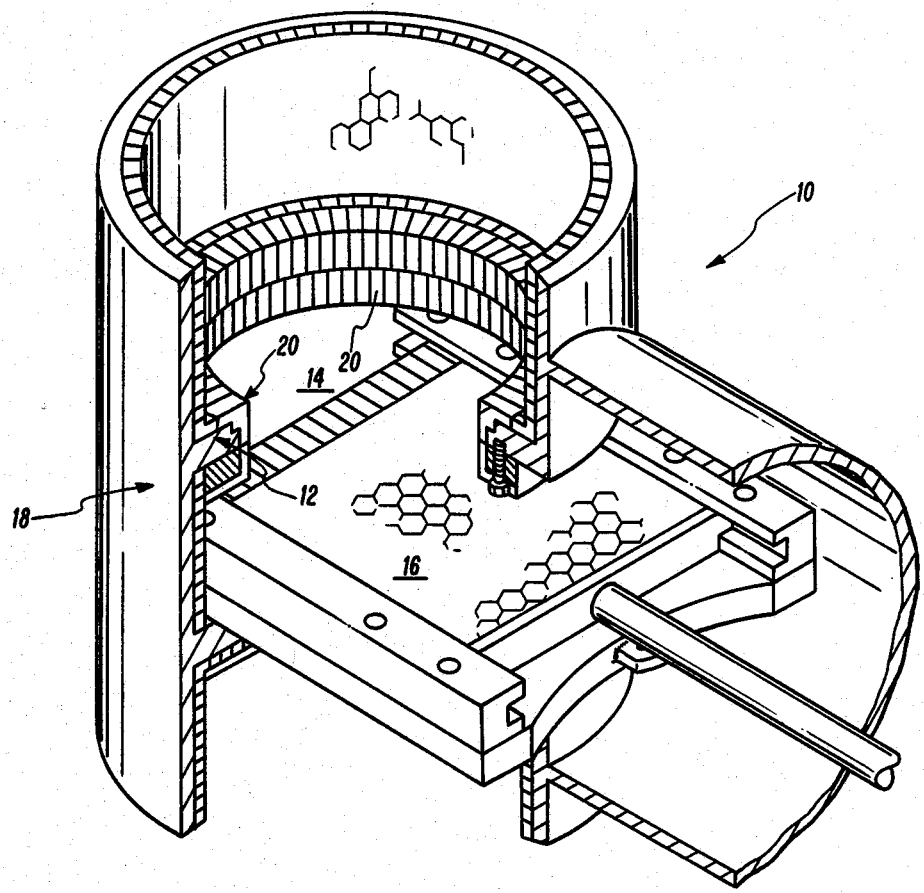
FIG. 1 is a perspective view, partly in section, of a single disc valve incorporating the wear sensor probe system of the present invention.

In the description which follows, like parts are marked throughout the specification and drawings with the same reference numerals, respectively. The drawings are not necessarily to scale and certain features of the invention may be exaggerated in scale or depicted in schematic form for illustration purposes in the interest of clarity and conciseness.

The term "wearable" as used herein denotes the tendency of a material to be eroded, worn away or otherwise deteriorated in response to fluid flow effects, including abrasion by solid particles entrained in a flow stream as well as including the effects of corrosion, impact and any other types of wear. Additionally, the term "integrity" as applied to a liner component or the like refers to structural completeness and absence of physical deterioration within a defined region of the component.

Referring now to FIG. 1, a high temperature valve 10 which is used in erosive/corrosive high temperature fluid flow environments has several components that are particularly vulnerable to rapid deterioration. These components include by way of example and not by way of limitation, a disc 12 having a central bore defining a flow passage 14 through which high temperature gases with entrained solid particles are conveyed. The valve body or shell 18 is constructed of high strength steel or equivalent material. Depending on the temperatures of the fluid flow within valve 10, the inner surface of valve shell 18 is protected by a composite liner component 20 of a thermally resistive refractory material such as ceramic or the like. The refractory lining is applied to the edges of the disc 12 which define an orifice within the flow passage 14, as well as to the edge surfaces of the slide 16 to prevent erosion of the underlying valve component parts.

The most serious erosion of the liner component occurs in the corner regions 22 and along the lining face 24 which define the orifice boundary. Thus it would be useful to know the condition of the liner component in this region, and of other such components which are subjected to severe erosion. Hereto it has been necessary to shut down the production process for inspection and repair or replacement of damaged liner components. However, upon implementation of the present invention, the wear condition of any flowline or valve component such as the refractory liner component 20 can be monitored continuously without halting or interfering in any way with the ongoing production operation.

Figure 2:
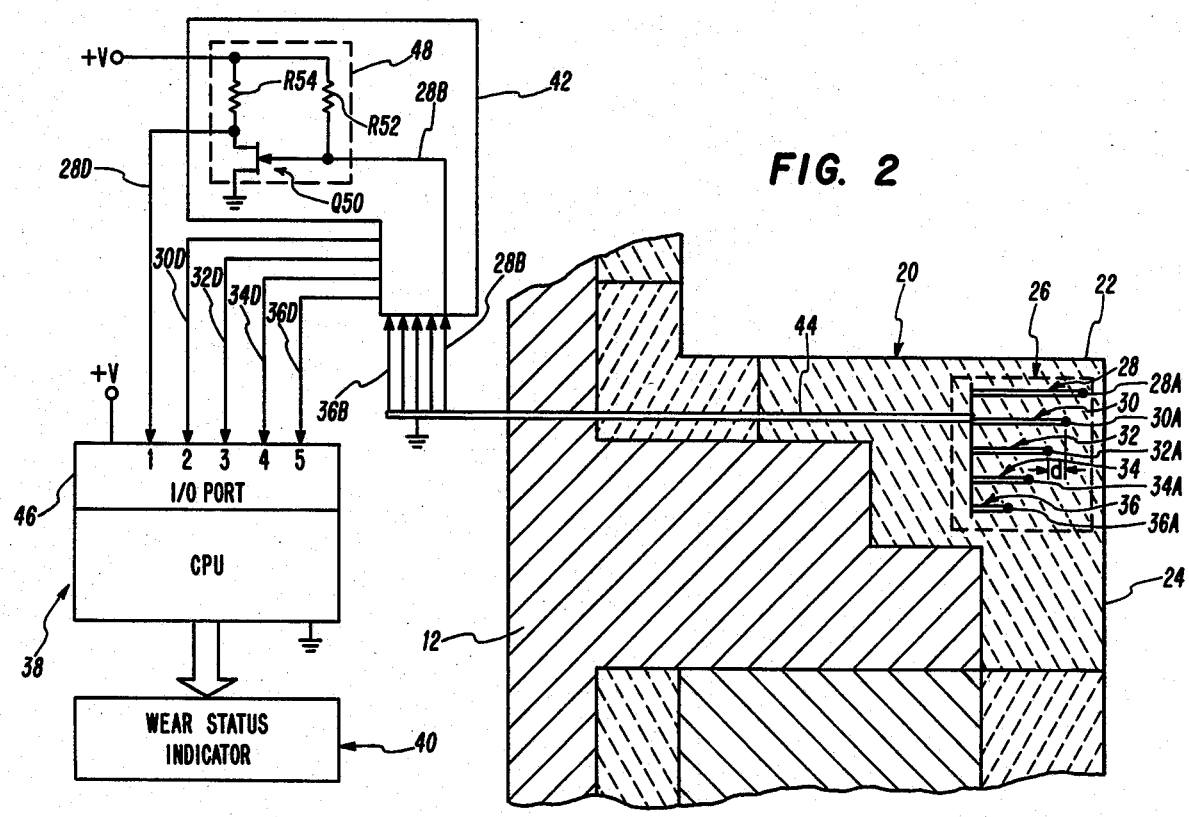
FIG. 2 is a simplified block diagram of the wear sensor system as incorporated in a valve liner component.

According to the present invention, real time wear condition data is provided by a wear sensor probe assembly 26 which includes multiple conductive loops 28, 30, 32, 34 and 36. Each conductive loop includes a wearable conductive portion 28A, 30A, 32A, 34A and 36A, represented symbolically in FIG. 2.

Each conductive loop and it wearable conductive portion is embedded at a predetermined location within the liner component 20. It will be noted that the conductive loop portions are spaced apart by a distance "d" within the corner region 22. As erosion of the liner component 20 is sustained, the conductive loops 28, 30, 32, 34 and 36 are subjected to erosion one at a time, with the wearable conductive loop portions 28A, 30A, 32A, 34A and 36A being interrupted only as the liner component structure is worn away at its particular location.

According to the method of the invention, the continuity status of each loop is evaluated periodically, with an electrical closed circuit condition of the loop indicating structural integrity of the liner component at the particular location of the corresponding wearable loop portion, and an electrical open circuit condition indicating liner erosion or damage at that particular probe location. In a preferred embodiment, the continuity status of each loop within the probe 26 is converted to logic one and logic zero digital data information which is sampled periodically by a CPU (indicated by reference numeral 38) for driving a wear status indicator 40 which provides a real time visual or audible indication in response to a predetermined wearable condition as detected by the probe 26, and which provides a printed summary of probe conditions upon demand. Additionally, the CPU 38 is programmed to analyze the probe data, and, under the direction of a controller, projects components and system failures as a function of time.

Figure 7:
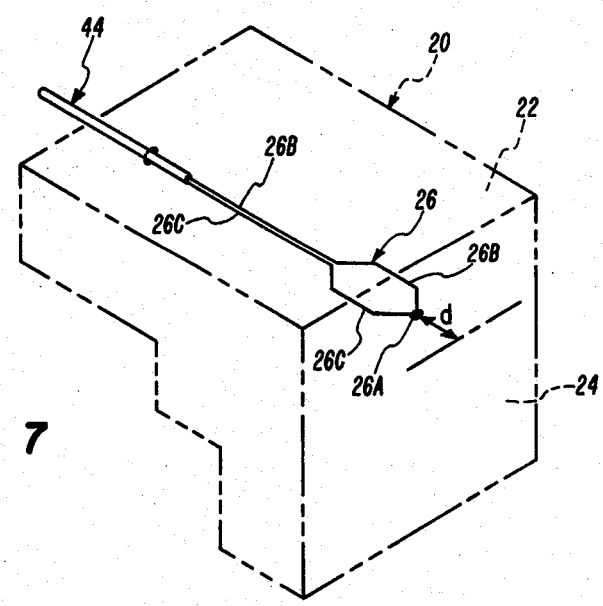
FIG. 7 is a perspective view of a wear sensor probe having a single conductive loop; and, FIG. 8 is a functional block diagram which illustrates the operation of a data processing system which has as one of its inputs a wear sensor probe assembly constructed according to the teachings of the present invention.

Referring now to FIG. 7, a generalized probe loop 26 is illustrated. This arrangement is typical for each of the conductive loops. Conductive loop 26 includes a wearable, conductive portion 26A, a signal conductor 26B and a return conductor 26C.

The wearable, conductive portion 26A is illustrated in FIG. 7 in the form of a bead. However, the wearable, conductive portion 26A may be an integral part of a continuous length of wire which constitutes the conductive loop. On the other hand, for certain applications, the end portions 26B, 26C of the conductive loop are joined to a bead of conductive, frangible material which has predictable erosion characteristics. One example of a preferred bead material is an alloy of tungsten which is relatively frangible with respect to the ceramic material in which it is embedded, and will undergo erosion at a faster rate relative to the refractory material, and thereby provide a reliable break indication as the surrounding refractory material is worn away at its location.

Alternatively, the bead 26A (or for that matter points 28A, 30A, 32A, 34A, 36A) may be a thermocouple junction which is formed by joining the positive 26B and negative 26C legs of a thermocouple. In the latter instance, the erosion sensor probe may be used to measure temperature at the inner wall surface and the integrity of the lining material may be detected by the presence or lack of a temperature signal from the thermocouple.

Figure 3:
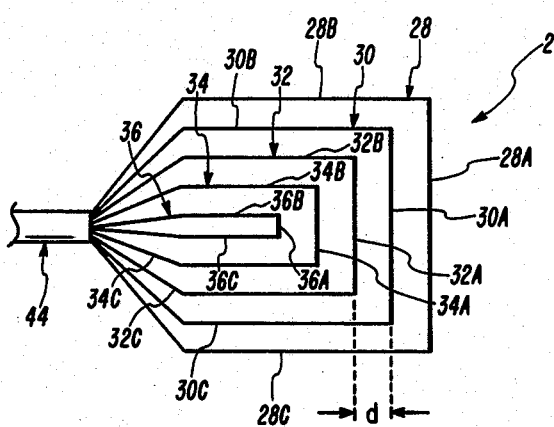
FIG. 3 is a simplified circuit diagram of a wear sensor probe having multiple conductive loops.
Figure 4:
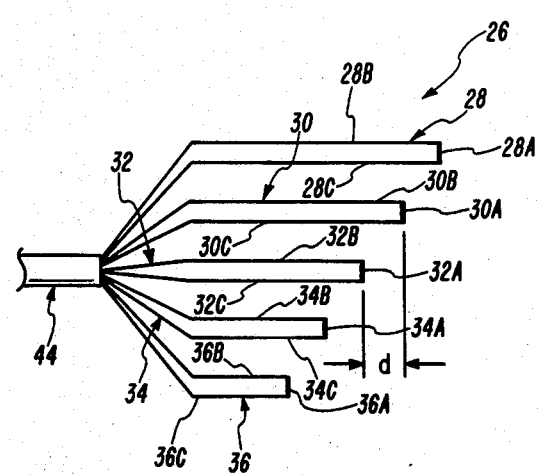
FIG. 4 is a simplified circuit diagram of an alternative embodiment of a wear sensor probe asembly having multiple conductive loops.
Figure 5:
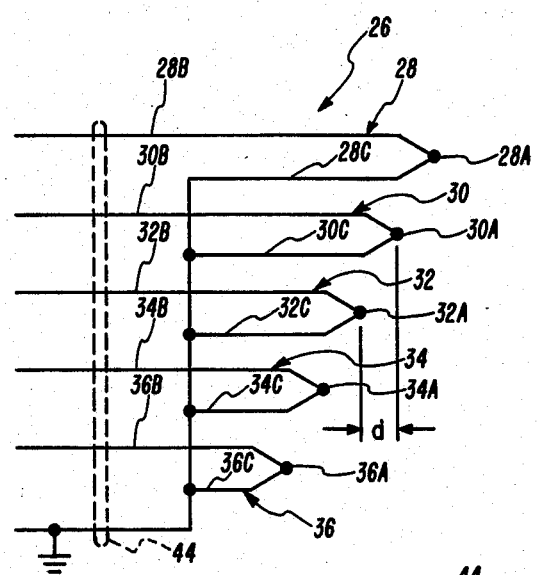
FIG. 5 is a simplified circuit diagram of a wear sensor probe assembly featuring an alternative arrangement for multiple conductive loops.

Variations in the size and arrangement of the conductive loops are illustrated in FIGS. 3, 4 and 5. However, the loops of each embodiment each comprise at least a signal conductor 26B and a return conductor 26C. In the arrangement shown in FIGS. 3, 4 and 5, each loop includes a wearable conductive portion which may or may not be structurally differentiated with respect to the signal and return conductors. That is, the conductive loop may comprise a continuous length of a conductive metal such as copper wire in which the wearable, conductive portions 28A, 30A, 32A, 34A and 36A are otherwise indistinguishable with respect to the signal conductors and return conductors, but are physically bent to produce the parallel segments as shown in FIGS. 3 and 4.

In the arrangement of FIG. 3, the parallel segments 28A, 30A, 32A, 34A and 36A generally diminish in size and are equally spaced by distance "d". An alternative arrangement is illustrated in FIG. 4 in which the segments 28A, 30A, 32A, 34A and 36A have equal lengths disposed in parallel and which are also spaced apart by distance "d".

In the arrangement illustrated in FIG. 5, the wearable conductive portion of each loop is represented symbolically by a dot or bead. In this arrangement, the signal and return conductors of each loop are joined in an angular union, with the dot or bead representing the vertex of the angular union of the two conductors. According to one arrangement, the signal conductor and return conductor are portions of a continuous length of conductor, with the dot representing the corner or vertex formed by the bend in the conductive loop. Alternatively, the signal and return conductors are joined together at the vertex by a bead of conductive material which is relatively frangible with respect to the component in which it is embedded.

While equal spacing between the respective wearable conductive portions within each probe is preferred, non-linear spacing arrangements can, for certain applications, be used to good advantage.

In each of the foregoing sensor arrangements, it is essential that a signal conductor be provided for each loop, and that at least one return conductor be provided. According to the arrangement shown in FIG. 5, the return conductors are connected together and are joined to a common return conductor which is coupled to a common ground reference potential. Additionally, although the wearable conductive portions are illustrated as straight segments in FIGS. 3 and 4, in some instances it is desirable that the segments be curved or otherwise shaped or conformed to match the geometry of the component flow stream surface which is subject to corrosion and erosion.

The open circuit/closed circuit condition of the conductive loop within the probe assembly 26 forms the basis for generating a digital data signal in the form of a logic "one" or a logic "zero" which corresponds with the condition of a particular loop as being in open circuit condition or closed circuit condition. Initially, each loop is in the closed circuit condition with the wearable conductive loop portion being intact. The open circuit condition established in response to the conductive loop portion being interrupted by the effects of erosion. This closed circuit/open circuit condition is converted to a logic "one" signal or a logic "zero" signal by a digitizer circuit 42.

The signal conductors and ground conductors are routed to the digitizer circuit 42 in a bundle 44 through the liner component and through the valve shell 18. Appropriate feed-through devices (not illustrated) are incorporated to seal the valve shell 18. The various signal conductors 28B, 30B, 32B, 34B and 36B form inputs to the digitizer 42. The output of the digitizer 42 is applied to I/O data input port 46 through output conductors 28D, 30D, 32D, 34D and 36D.

By way of example and not by limitation, an appropriate digitizer circuit which is utilized to produce the logic "one" and logic "zero" digital data signals is the inverter circuit 48 having a field effect transistor (FET) switch Q50 and two currentlimiting resistors R52 and R54. More elaborate digitizing circuitry may be used as desired. In the foregoing example, the loop signal conductor 28B forms an input to the gate of Q50. The base and source electrodes of Q50 are coupled to a voltage source V through the current limiting resistors R52, R54, respectively, and the source electrode of Q50 is connected to ground reference potential.

In the circuit closed condition of probe loop 28, the gate of Q50 is connected to ground reference potential, which maintains the transistor switch Q50 in off condition. In off condition, the drain electrode rises to +V potential, which is defined as logic "one". A logic one signal (+V) is maintained on output conductor 28D at I/O port 1 for as long as the sensor probe loop 28 is in closed circuit condition. When the continuity of probe loop 28 is interrupted, the ground circuit to the gate of Q50 is broken and the potential applied to the gate of transistor switch Q50 rises to +V volts, causing transistor switch Q50 to turn on, thereby shorting the output conductor 28D through the source elctrode to ground potential, which has previously been defined as logic "zero" condition. The logic "zero" condition (i.e. ground potential) is maintained at the input of I/O port 1 for as long as the sensor probe loop 28 is interrupted. A separate inverter circuit 48 is provided for each separate loop signal conductor 28B, 30B, 32B, 34B and 36B.

Figure 6:
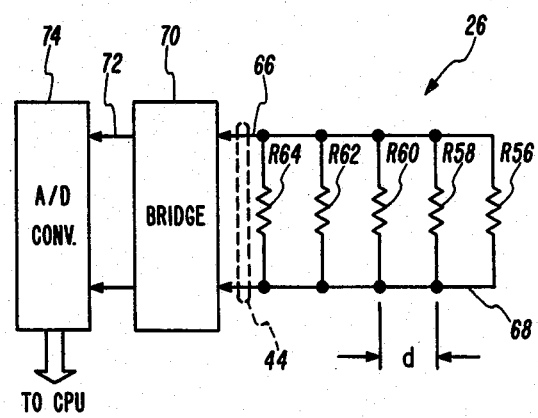
FIG. 6 is a simplified circuit diagram of an alternative wear sensor probe in which multiple resistor elements are connected in parallel.

An alternative wear sensor probe 26 is illustrated in FIG. 6. According to this alternative embodiment, the wearable, conductive loop portions are in the form of resistors R56, R58, R60, R62 and R64. These resistors are connected in parallel relation and are spaced apart by a distance d. Conductors 66, 68 connect the parallel resistor array to a bridge circuit 70. The bridge circuit 70 produces an output impedance signal 72 which is porportional to the impedance of the parallel connected resistor group. The impedance signal 72 increases incrementally from a nominal impedance $Z_o$ to infinity as the resistive link portions R56, R58, R60, R62 and R64 are eroded away, one by one.

The impedance signal 72 forms an input to an analog-to-digital converter 74 which produces a digital data word corresponding to the magnitude of the impedance signal 72. That is, a different digital data word is developed according to the number of conductive elements R56, R58, R60, R62 and R64 which are intact and operable at the time the measurement is made. The output of the analog-to-digital converter 74 is scanned by the CPU 38 according to a predetermined schedule and generates a digital data word representative of the overall impedance status of the probe 26. Each digital data word produced is unique and corresponds with the exact number of intact, operable resistor links remaining in the probe. This information is supplied to the wear status indicator which provides an alarm or provides a printed summary of probe conditions as desired.

An alternative statement of the foregoing relation is that the conductivity of the overall probe assembly 26 diminishes incrementally from a nominal value $G_o$ to zero as each of the resistors R56, R58, R60, R62 and R64 are worn away, one by one, in response to the effects of erosion.

Figure 8:
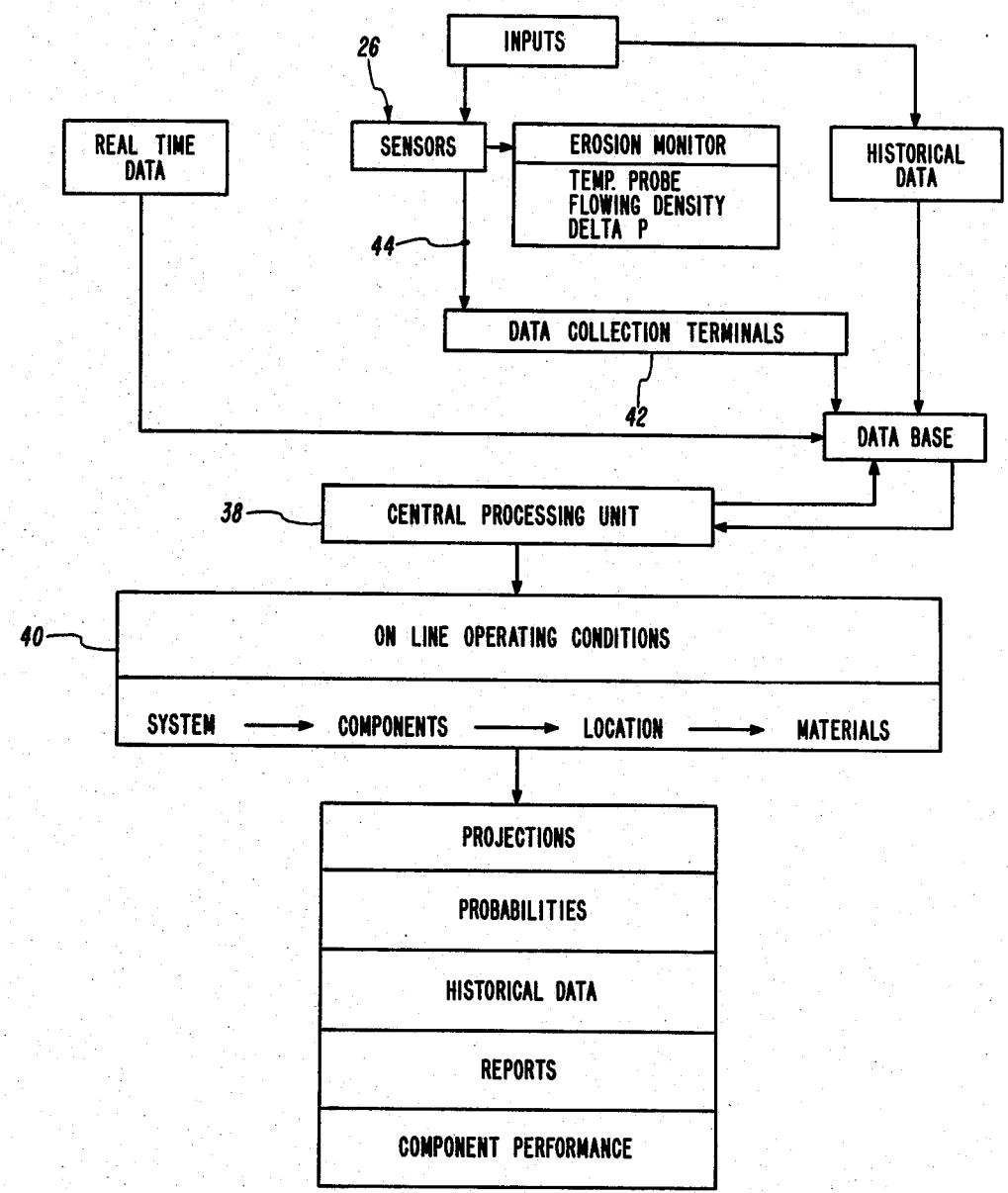

In operation, the CPU scans the I/O ports 1, 2, 3, 4, 5 according to a predetermined schedule and generates a digital data word representative of the continuity status of each loop within a particular probe assembly. This data is applied to the wear status indicator which, operating under the direction of a controller provides a visual or audible alarm, or provides a printed summary of probe conditions upon request, as illustrated by FIG. 8.

Although the invention has been described with reference to specific embodiments, and with reference to a specific high temperature valve application, the foregoing description is not intended to be construed in a limiting sense. Various modifications of the disclosed embodiments as well as alternative applications of the invention will be suggested to persons skilled in the art by the foregoing specification and illustrations. For example, the probe assembly of the present invention can be incorporated with other structures and materials which are subjected to the effects of wear, erosion or corrosion, such as a pressure vessel in which caustic fluids are contained, lines, vessels, cyclones, deflectors, chutes, nozzles and other wear and erosion prone areas of either refractory, ceramic, plastic, rubber or other like materials. It is therefore contemplated that the appended claims will cover any such modifications or embodiments that fall within the true scope of the invention.

We claim:

1. Apparatus for detecting a wearable condition of a component comprising:
  a wear sensor probe including at least one conductive loop embedded within said component; and,
  means coupled to said wear sensor probe for determining the continuity status of said conductive loop;
  said at least one conductive loop having a signal conductor portion, a return conductor portion and a wearable, conductive segment connected in electrical series relation with said signal conductor portion and said return conductor portion, said wearable, conductive segment being relatively frangible with respect to the component in which it is embedded.

* * * * *